United States Patent
Lindenthaler

(10) Patent No.: US 10,974,046 B2
(45) Date of Patent: *Apr. 13, 2021

(54) SYSTEM AND METHOD FOR EYELID STIMULATION

(71) Applicant: MED-EL Elektromedizinische Geraete GmbH, Innsbruck (AT)

(72) Inventor: Werner Lindenthaler, Oberperfuss (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 161 days.

This patent is subject to a terminal disclaimer.

(21) Appl. No.: 16/270,024

(22) Filed: Feb. 7, 2019

(65) Prior Publication Data

US 2019/0167473 A1  Jun. 6, 2019

Related U.S. Application Data

(60) Continuation of application No. 15/291,162, filed on Oct. 12, 2016, now Pat. No. 10,219,937, which is a
(Continued)

(51) Int. Cl.
*A61N 1/36* (2006.01)
*A61F 9/007* (2006.01)
(Continued)

(52) U.S. Cl.
CPC ...... *A61N 1/36003* (2013.01); *A61F 9/00718* (2013.01); *A61H 23/00* (2013.01); *A61H 23/02* (2013.01); *A61N 1/36031* (2017.08); *A61N 1/36034* (2017.08); *A61N 1/36046* (2013.01); *A61N 1/36057* (2013.01); *A61N 1/36067* (2013.01); *A61N 1/36139* (2013.01);
(Continued)

(58) Field of Classification Search
None
See application file for complete search history.

(56) References Cited

U.S. PATENT DOCUMENTS 5,360,438 A  11/1994 Fisher
5,897,579 A   4/1999 Sanders
(Continued)

FOREIGN PATENT DOCUMENTS

WO   2010048261 A1   4/2010

OTHER PUBLICATIONS

International Searching Authority, International Search Report and Written Opinion, International Application No. PCT/US2012/069790, dated Feb. 20, 2013, 13 pages.
(Continued)

*Primary Examiner* — Michael W Kahelin
(74) *Attorney, Agent, or Firm* — Sunstein LLP

(57) ABSTRACT

A system and method of treating hyperactivity of an eyelid closing muscle in a subject includes providing a stimulation system in the subject with the hyperactivity of the eyelid closing muscle, sensing an activity of the eyelid closing muscle, and selectively stimulating eyelid opening muscle(s) or innervating nerves, eyelid opening reflexes, or eyelid opening reflexes in non-muscular tissue, using the stimulation system, without substantially activating the eyelid closing muscle. The system and method evokes eyelid movement in the subject.

7 Claims, 6 Drawing Sheets

Related U.S. Application Data continuation of application No. 15/017,769, filed on Feb. 8, 2016, now Pat. No. 9,492,346, which is a continuation of application No. 14/590,158, filed on Jan. 6, 2015, now Pat. No. 9,254,239, which is a continuation of application No. 14/289,979, filed on May 29, 2014, now Pat. No. 8,934,982, which is a division of application No. 13/714,900, filed on Dec. 14, 2012, now Pat. No. 8,781,594.

(60) Provisional application No. 61/570,409, filed on Dec. 14, 2011.

(51) Int. Cl.
*A61H 23/00* (2006.01)
*A61H 23/02* (2006.01)

(52) U.S. Cl.
CPC ........ *A61H 23/004* (2013.01); *A61H 23/0245* (2013.01); *A61H 2201/501* (2013.01); *A61H 2201/5012* (2013.01); *A61H 2201/5097* (2013.01); *A61H 2205/024* (2013.01)

(56) References Cited

U.S. PATENT DOCUMENTS

| | | |
|---|---|---|
| 6,792,314 B2 | 9/2004 | Byers et al. |
| 7,684,858 B2 | 3/2010 | He et al. |
| 8,781,594 B2 | 7/2014 | Lindenthaler |
| 8,934,982 B2 | 1/2015 | Lindenthaler |
| 9,254,239 B2 | 2/2016 | Lindenthaler |
| 9,492,346 B2 | 11/2016 | Lindenthaler |
| 2003/0176898 A1 | 9/2003 | Gross et al. |
| 2006/0135319 A1 | 6/2006 | Berman |
| 2009/0306454 A1 | 12/2009 | Cockerham et al. |

OTHER PUBLICATIONS

European Patent Office, Extended European Search Report, Application No. 12858112.1-1652, dated Jun. 5, 2015, 5 pages.

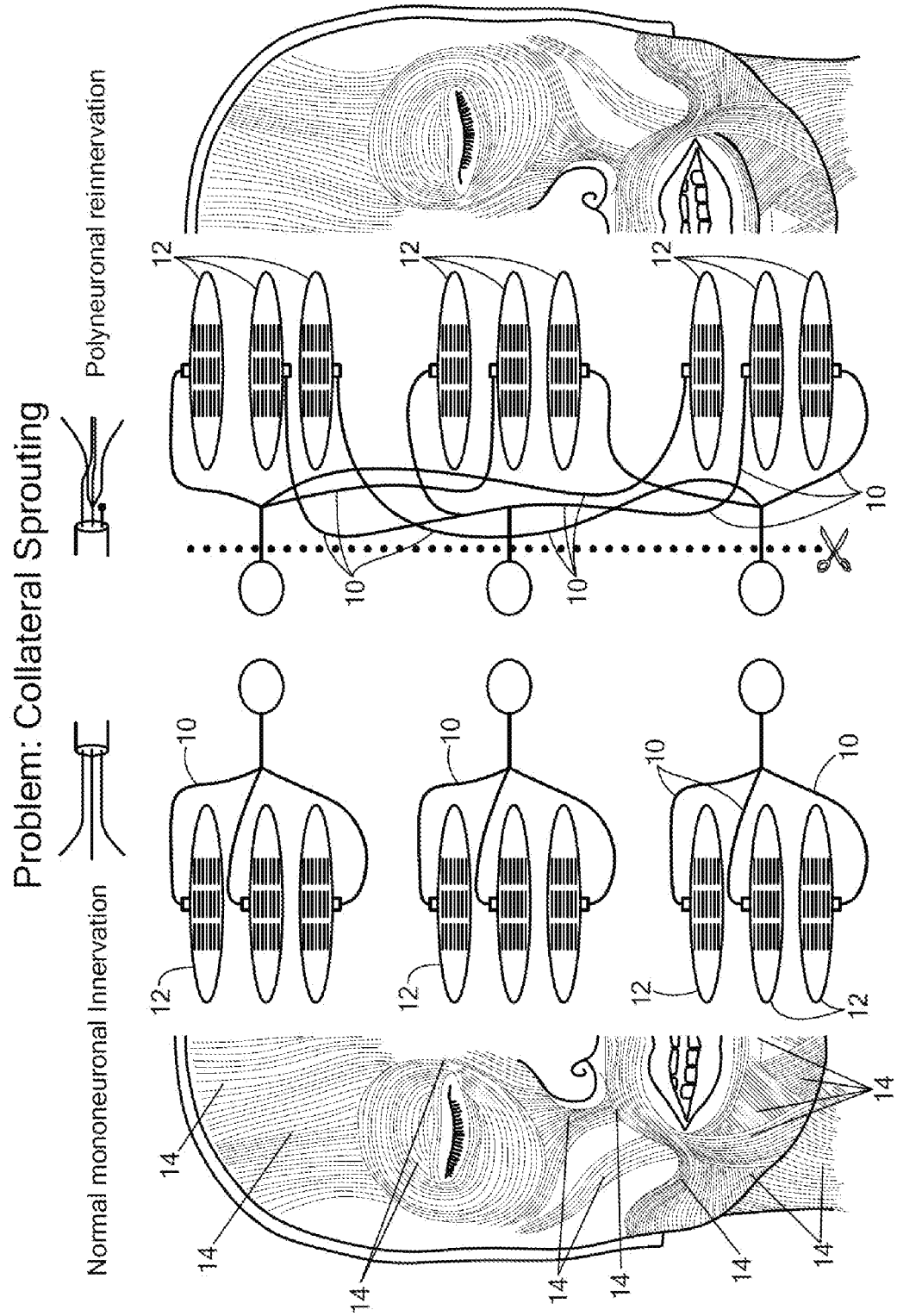

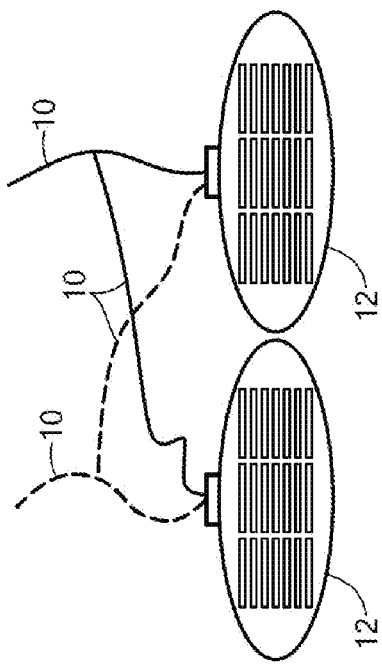
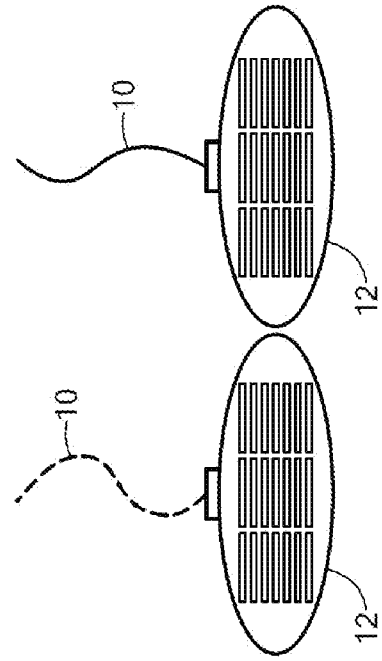

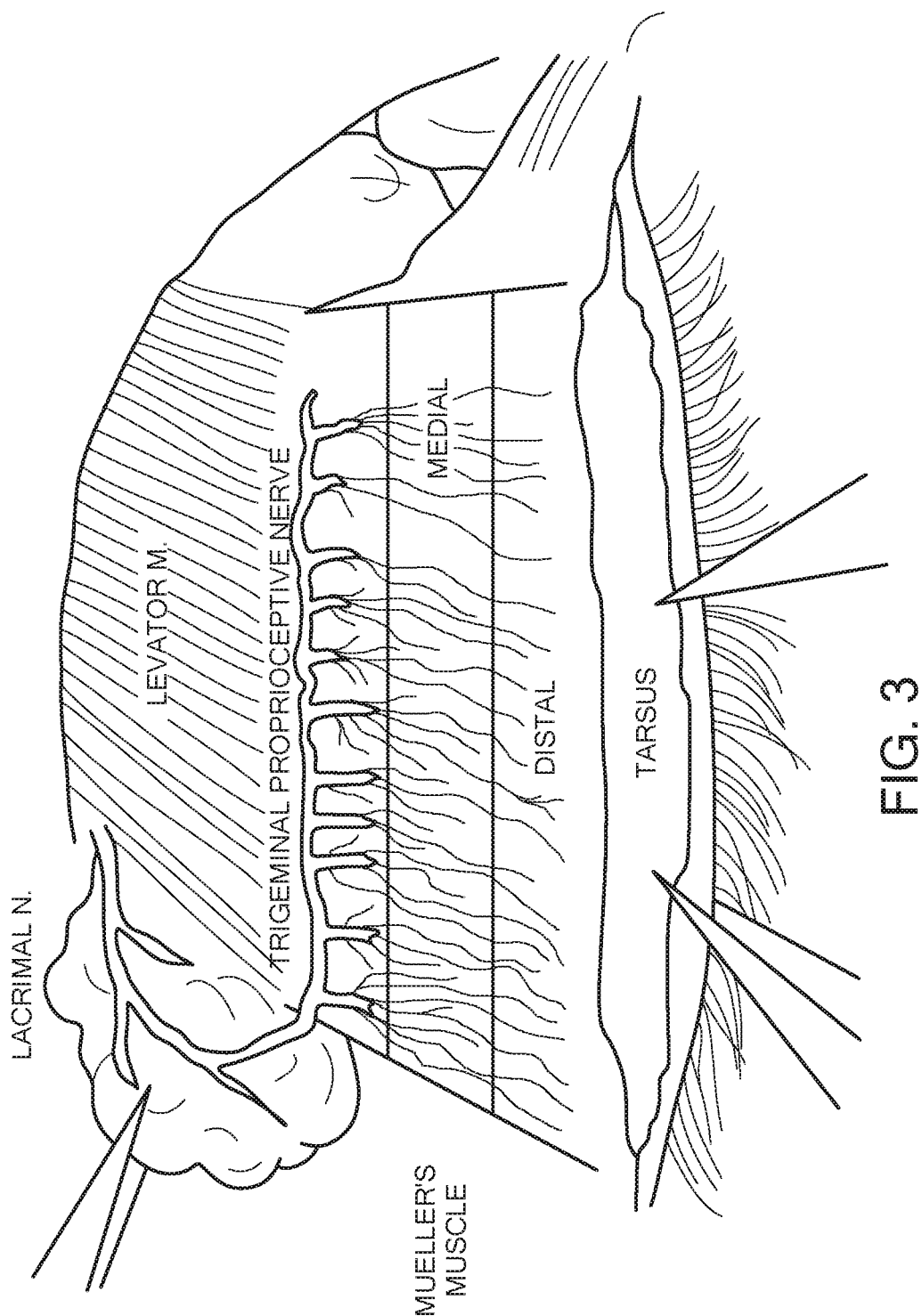

SYSTEM AND METHOD FOR EYELID STIMULATION

CROSS REFERENCE TO RELATED APPLICATIONS

The present application is a continuation of U.S. patent application Ser. No. 15/291,162 filed Oct. 12, 2016, which is a continuation of U.S. patent application Ser. No. 15/017,769 filed Feb. 8, 2016, now U.S. Pat. No. 9,492,346, which is a continuation of U.S. patent application Ser. No. 14/590,158 filed Jan. 6, 2015, now U.S. Pat. No. 9,254,239, which is a continuation of U.S. patent application Ser. No. 14/289,979 filed May 29, 2014, now U.S. Pat. No. 8,934,982, which is a divisional of U.S. patent application Ser. No. 13/714,900 filed Dec. 14, 2012, now U.S. Pat. No. 8,781,594, which claims the benefit of U.S. Provisional patent application No. 61/570,409 filed Dec. 14, 2011, the disclosures of which are incorporated by reference herein in their entirety.

TECHNICAL FIELD

The invention generally relates to stimulation methods and systems and, more particularly, the invention relates to eyelid stimulation.

BACKGROUND ART

There are various articles describing eyelid opening and closing mechanisms and the related eyelid structures involved. For example, one article describes the stretching of the Mueller muscle which results in involuntary contraction of the levator muscle (K. Matsuo, *Ophthal Plast Reconstr Surg*, 18(1), 2002 January, p. 5-10). Another article describes the refined distribution of myelinated trigeminal proprioceptive nerve fibers in Mueller's muscle as the mechanoreceptors to induce involuntary reflexive contraction of the levator and frontalis muscles (S. Yuzuriha, K. Matsuo, C. Hirasawa, T. Moriizumi, *J Plast Reconstr Aesthet Surg*, 62(11), 2009 November, p. 1403-1410). Another article describes the reflexive contraction of the levator palpebrae superioris muscle to involuntarily sustain the effective eyelid retraction through the transverse trigeminal proprioceptive nerve on the proximal Mueller's muscle, and its verification with evoked electromyography (R. Ban, K. Matsuo, Y. Osada, M. Ban M, S. Yuzuriha, *J Plast Reconstr Aesthet Surg*, 63(1), 2010 January, p. 59-64). Another article describes the efferent and afferent innervations of Mueller's muscle related to the involuntary contraction of the levator muscle, which is important for avoiding injury during eyelid surgery (S. Yuzuriha, K. Matsuo, Y. Ishigaki, N. Kikuchi, K. Kawagishi, T. Moriizumi, *Br J Plast Surg*, 58(1), 2005 January, p. 42-52). All of the above articles are hereby incorporated by reference in their entirety.

Some problems encountered with eyelid opening and closing mechanisms may be caused by unilateral damage of the nerve fibers of the facial nerve or its nucleus which leads to peripheral facial paresis. In Western Europe and the USA, the incidence of peripheral facial pareses is approx. 20-35/100,000 inhabitants. Thus, facial paresis is a common disease. In most cases and depending on the cause, peripheral paresis shows non-degenerative paresis (neurapraxia according to Seddon) so that 80% of the cases show regeneration of the nerve under adequate therapy. 95% of cases with central facial paresis show regeneration. In cases of degenerative paresis (axonotmesis, neurotmesis, mixed forms according to Seddon) caused by the destruction of nerve fibers, persistent defects are observed after healing.

Persistent defects after healing are even observed in cases of spontaneous regeneration or optimal and extensive surgical reconstruction of the nerve in cases of nerve transsection and bridging of the defect with neural transplants. Sprouting of the regenerating axons is observed at the site of the lesion even after reconstruction of nerve continuity. At the same time, Wallerian degeneration of the entire affected section of the nerve as far as the muscles is completed until only the Bungner's bands remain as Schwann cell conducting structures. The regenerating neurons with their sprouting axons grow accidentally into these bands of the individual nerve branches and are directed to the peripheral mimic muscles. Individual axons perish and do not reach the periphery, some accidentally reach their original target muscle, while others reach a completely different target muscle. Due to axonal collateral sprouting, the most frequently observed effect is simultaneous sprouting to several target muscles, such as shown in FIGS. 1A and 1B.

This leads clinically to simultaneous movement of several target muscles (a condition called synkinesis). Patients often complain about involuntary lid closure while moving the mouth, e.g., when eating. Simultaneous movement of antagonist muscles leads to the autoparalytic syndrome: muscle forces cancel each other out and no movement is observed clinically despite innervation. New research shows that not only collateral sprouting but also terminal sprouting (such as shown in FIGS. 2A and 2B) of the regenerating axons directly at the neuromuscular end-plates causes uncoordinated muscle function. This explains why the patients' quality of life is significantly limited even after surgical reconstruction of the nerve. If the lesion is so extensive that the remaining peripheral part of the facial nerve is insufficient, or if Bungner's bands are fibrosed due to failed reinnervation and muscles are atrophied due to long term denervation of more than 3 to 5 years, the patient can no longer be offered a nerve graft. Possible therapies include dynamic muscle grafts, free nerve-muscle transplantation, implantation of upper lid weights or static suspensions. Functional results of these secondary procedures are even less satisfactory than the above mentioned nerve grafts. These procedures may, at best, restore muscle tone, but facial expression remains very mask-like and the dynamic muscle suspensions allow only few and very mechanistic movement vectors to be reproduced.

There are basically three classes of symptoms in facial nerve paralysis that may affect eyelid closure. First, a complete loss of the peripheral facial nerve leads to a loss of muscle tone in the affected half of the face or of the area innervated by the lost peripheral facial nerve branch and the soft tissues of the face sag. Voluntary motor movement is lost, and mimic muscles can no longer be moved. The inability to close the eyelid indirectly leads to vision disorders since the eye waters and inflammation is possible. This hypo-eyelid-closure problem affects less than 20% of patients.

Second, a pronounced but synkinetic reinnervation leads to the simultaneous movement of several target muscles. As mentioned above, patients may experience involuntary lid closure, e.g., while moving the mouth, or simultaneous movement of antagonist muscles which leads to the muscle forces cancelling each other out. This disynergic-eyelid-closure problem affects greater than 30% of patients.

Third, peripheral polyinnervation, central poly-activation or central hypo-inhibition, may lead to an almost continuous contraction of a muscle, like in a tremor, spasm or spasmodic pathogenesis. This hyperactivity of the musculus orbicularis oculi or hyper-eyelid-closure problem affects greater than 30% of patients. There are some therapies adapted for hyper-contractions of a muscle that may be used in eyelid closure. These therapies focus on pathologically weakening the hyper-contracted or hyper-activated muscles that are involved in the tremor or spasm. For example, botulinum toxin may be injected in contracting muscles to temporarily damage nerve-muscle transfer of some of the synapses of the contracting muscles. Alternatively, some percentage of nerve fibers innervating the contracting muscle, or some percentage of the muscle fibers of the contracting muscle, may be surgically damaged.

SUMMARY OF EMBODIMENTS

In accordance with one embodiment of the invention, a method of treating hyperactivity of an eyelid closing muscle in a subject includes providing a stimulation system and selectively stimulating one or more eyelid opening muscles or innervating nerves, using the stimulation system, without substantially activating the eyelid closing muscle, thereby evoking eyelid movement in the subject.

In accordance with another embodiment of the invention, a method of treating hyperactivity of an eyelid closing muscle in a subject includes providing a stimulation system in the subject with the hyperactivity of the eyelid closing muscle, sensing an activity of the eyelid closing muscle, and selectively stimulating one or more eyelid opening reflexes in muscles, using the stimulation system, without substantially activating the eyelid closing muscle, thereby evoking eyelid movement in the subject.

In accordance with another embodiment of the invention, a method of treating hyperactivity of an eyelid closing muscle in a subject includes providing a stimulation system and selectively stimulating one or more eyelid opening reflexes in non-muscular tissue, without substantially activating the eyelid closing muscle, thereby evoking eyelid movement in the subject.

In accordance with related embodiments, stimulating may include electrical stimulation, mechanical stimulation, and/or vibratory stimulation. The eyelid opening muscles may include levator muscle and/or frontal muscle. Stimulated levator muscle may include slow-twitch muscle fibers and/or fast-twitch muscle fibers. Stimulating eyelid opening reflexes in muscles may include stimulating levator fast-twitch muscle fibers to cause activation of mechanoreceptors in Mueller's muscle and intermuscular connective tissues leading to an involuntary continuous contraction of levator slow-twitch muscle fibers. Stimulating eyelid opening reflexes in muscles may include stimulating transverse nerve fibers to induce involuntary contraction of levator muscle and Mueller's muscle. Stimulating eyelid opening reflexes in muscles may include stimulating sympathetic γ efferent nerve fibers to increase efferent sympathetic tone thereby increasing the rate of involuntary tonic contraction of the muscles. Movement may be opening or closing of the eyelid. When opening the eyelid, the opening may be caused by retraction of the eyelid against gravity and may be maintained by involuntary continuous contraction of the levator slow-twitch muscle fibers as a result of proprioception. The eyelid movement may be caused by shortening a distal part of the Mueller muscle due to the increased efferent sympathetic tone. Stimulating eyelid opening reflexes in non-muscular tissue may include stimulating I-a proprioceptive afferent nerve connecting a mechanoreceptor of intermuscular connective tissues among middle and distal Mueller's smooth muscle fibers with motor nucleus to induce involuntary contraction of levator muscle and Mueller's muscle. Stimulating eyelid opening reflexes in non-muscular tissue may include stimulating intermuscular connective tissues among middle and distal Mueller's smooth muscle fibers to induce reflexive contraction.

In accordance with another embodiment of the invention, a stimulation system for treating hyperactivity of an eyelid closing muscle in a subject includes a processor having program code for generating at least one stimulation parameter that is used to stimulate one or more eyelid opening muscles or innervating nerves of the subject, and a stimulator configured to receive the stimulation parameter and to stimulate the one or more eyelid opening muscles or innervating nerves based on the stimulation parameter. Alternatively, or in addition, the stimulation parameter may be used to stimulate one or more eyelid opening reflexes in muscles and/or may be used to stimulate one or more eyelid opening reflexes in non-muscular tissue.

In accordance with related embodiments, the stimulation system may further include an activating switch, in communication with the processor, configured to generate a first signal. The processor has program code for receiving the first signal and for generating the at least one stimulation parameter based on the first signal. The activating switch may automatically activate the stimulation system based on various sensed parameters or may manually activate the system. For example, the activating switch may be a sensing electrode configured to detect activity of the eyelid closing muscle and/or the activating switch may be a manual activator operable by the subject. The processor may be configured to receive the first signal by inductive coupling, capacitive coupling, electromagnetic transmission, light coupling, vibratory coupling, mechanical coupling and/or acoustical coupling.

BRIEF DESCRIPTION OF THE DRAWINGS

The foregoing features of the invention will be more readily understood by reference to the following detailed description, taken with reference to the accompanying drawings, in which:

FIG. 1A shows a diagram of normal somatotopic organization of facial innervation and FIG. 1B shows the condition after lesion of the facial nerve;

FIG. 2A shows a diagram of a normal end-plate region on a muscle fiber and FIG. 2B shows a diagram of end-plates activated by several axons due to terminal sprouting;

FIG. 3 shows a schematic illustration of Müller's muscle;

DESCRIPTION OF ILLUSTRATIVE EMBODIMENTS

Figure 4:
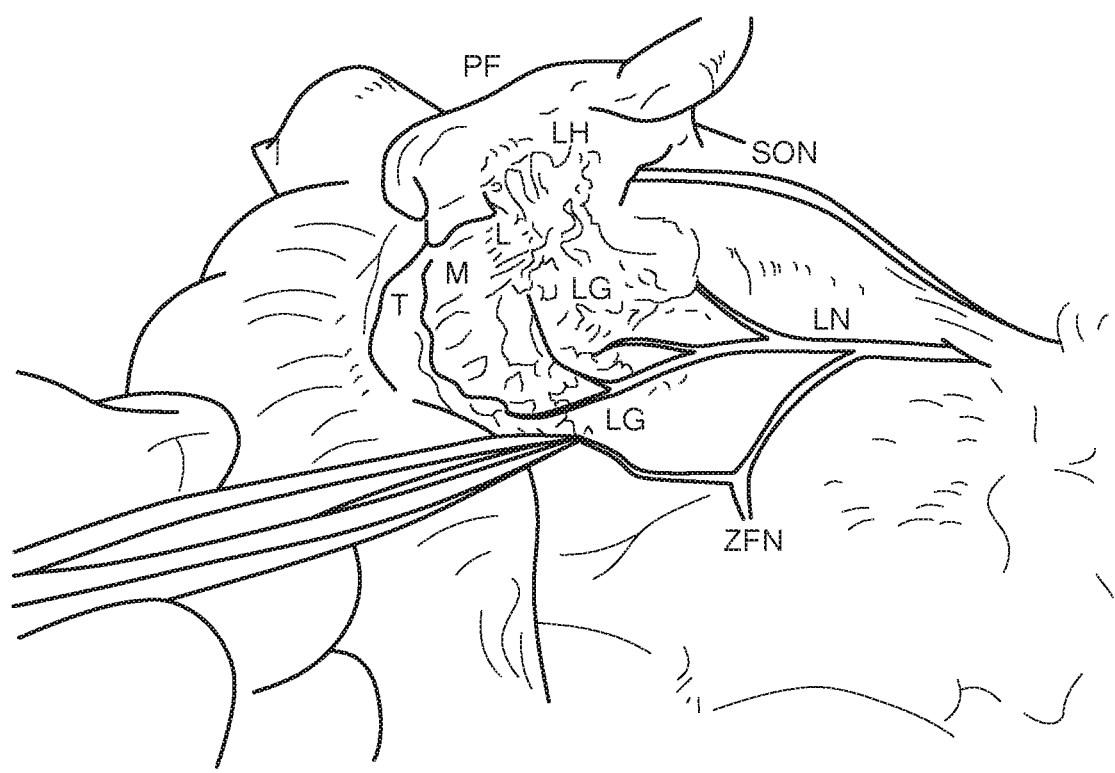
FIG. 4 shows a schematic illustration of the innervation of Müller's muscle.

The present invention is directed to a system and method of eyelid stimulation that selectively activates the eyelid opening muscle(s) (levator, levator palpebrae superioris muscle, and frontalis muscles) without activating the eyelid closing muscle(s). The activation may include stimulation of one or more of the eyelid opening muscles or innervating nerves, the eyelid opening reflexes in muscles, and/or the eyelid opening reflexes in non-muscular tissue. For example, the muscle fibers or the innervating nerves of the levator muscle or the frontalis muscle may be stimulated. Alternatively, or in addition, the fast-twitch muscle fibers of the levator muscle may be stimulated to cause activation of mechanoreceptors in Mueller's muscle and intermuscular connective tissues, leading to an involuntary, continuous contraction of levator slow-twitch muscle fibers in order to induce the eyelid movement in patients. Alternatively, or in addition, the transverse nerve fibers may be stimulated to induce involuntary contraction of both the levator muscle and Mueller's muscle in order to induce the eyelid movement in patients. Alternatively, or in addition, the sympathetic γ efferent nerve fibers, or via the superior cervical ganglion, may be stimulated to increase efferent sympathetic tone to increase the rate of involuntary tonic contraction of the muscle(s) causing the eyelid movement in patients. Alternatively, or in addition, the I-a proprioceptive afferent nerve connecting the mechanoreceptor of the intermuscular connective tissues among the middle and distal Mueller's smooth muscle fibers with the motor nucleus may be stimulated to induce involuntary contraction of both the levator muscle and Mueller's muscle. Alternatively, or in addition, the intermuscular connective tissues among the middle and distal Mueller's smooth muscle fibers may be stimulated to induce reflexive contraction of the eyelid opening muscles. In all cases, the stimulation may be electrical stimulation, mechanical stimulation and/or vibratory stimulation of the muscles, nerves, and/or reflexes.

In patients with synkinetic reinnervation after facial nerve paralysis, the synkinetic reinnervation and polyinnervations may lead to an almost continuous contraction of a muscle, exhibiting symptoms like in a tremor, spasm or spasmodic pathogenesis. This condition is not very well understood and standard therapies and procedures focus on the symptoms of the continuous contraction of the muscle. The consensus is that stimulation of any part of the patient's affected facial nerve system should be avoided so that the symptoms are not made worse. Instead, standard therapies focus on pathologically weakening the hyper-contracted or hyper-activated muscles involved in the tremor or spasm. In patients with eyelid closure issues, the general belief is that the tremor-like, spasm-like, or spasmodic-like pathogenesis is a tremor or spasm of all muscles attached to the eyelid (e.g., openers, closers, tensors) where activation of some part of the tremor-, spasmodic-system bears a high risk of increasing the contraction of muscles involved in the tremor or spasm.

Embodiments of the present invention, however, discovered that selectively focusing stimulation on the contraction of muscles opening or elevating the eyelid without causing any contraction of the eyelid closing muscles, overcame these tremor-like symptoms. This was due to fact that the net closing force of the tremor- or spasmodic-like activated closing muscle(s) is overcome and compensated by the net opening force of one or more of the eyelid opening muscles. Since the eye closing muscles are innervated by a nerve (facialis) different than the eye opening muscles (trigeminus), embodiments of the present invention focus on activating the eyelid opening muscles(s) without activating the eyelid closing muscle(s). For example, the selective stimulation of one or more eyelid opening muscles or innervating nerves, eyelid opening reflexes in muscles, and/or eyelid opening reflexes in non-muscular tissue may compensate for the problem of hyper-eyelid-closure or hyperactivity of the musculus orbicularis oculi. Currently, there is no way of surgically or pharmaceutically activating antagonists of hyper-contracting eyelid closing muscles to compensate for the hyper-closure by appropriate contraction of eyelid opening muscle(s). Thus, the selective stimulation of eyelid opening muscles using electrical, mechanical and/or vibratory methods, according to embodiments of the present invention, provides a valuable treatment solution for patients with these kinds of problems.

There are several eyelid opening muscles that help to open the eyelid, the levator muscle, levator palpebrae superioris muscle, and frontalis muscles. The levator muscle is innervated by the central caudal nucleus of the oculomotor nuclear complex and is a skeletal muscle which originates from the orbital bone and transforms into the levator aponeurosis. The deep expansion of this aponeurosis inserts into the anterior surface of the tarsus, the middle expansion into the pretarsal orbicularis oculi muscle, and the superficial expansion becomes the orbital septum. Thus, contraction of the levator muscle retracts the tarsus, the pretarsal orbicularis oculi muscle and skin, and the lateral orbital fat pad by means of the expansions of the levator aponeurosis. As shown in FIG. 3, the Mueller muscle, on the other hand, which is innervated by the sympathetic efferent via the superior cervical ganglion, is a smooth muscle, which originates from the undersurface of the levator muscle and inserts onto the superior border of the tarsus. Because the levator muscle fibers do not surround the Mueller muscle fibers and lie in series with them, contraction of the levator muscle stretches the Mueller muscle along with the levator aponeurosis.

FIG. 4 shows the gross anatomy of the innervations of Mueller's muscle. A fine transverse nerve is accompanied by the peripheral arcade (arrow), and other nerves that run between the distal portion of the levator muscle and the proximal portion of Mueller's muscle (arrow heads) pass through the lacrimal gland to join the lacrimal nerve. In FIG. 4, T indicates the tarsus; M, Mueller's muscle; L, levator muscle; LH, lateral horn (turned up); PF, preaponeurotic fat; LG, lacrimal gland; SON, supraorbital nerve; LN, lacrimal nerve; ZFN, zygomatico-facial nerve.

In some cases, denervated muscle fibers may be innervated by more than one nerve fiber. In this case, the action potentials for contraction arrive from nerve fibers originally innervating muscle fibers for different functions (e.g., the antagonistic muscle). This polyinnervation—which may be due to the overlapping or disturbance of central projection areas of peripheral muscles in the brain—causes activation of muscle fibers during many more activities or functions than originally desired for a certain muscle. This situation may lead to an almost continuous contraction of the muscle (e.g., like in a tremor or spasm or spasmodic pathogenesis) in some cases. In situations such as this, a patients' quality of life may be significantly limited even after surgical reconstruction of the nerve.

Figure 5:
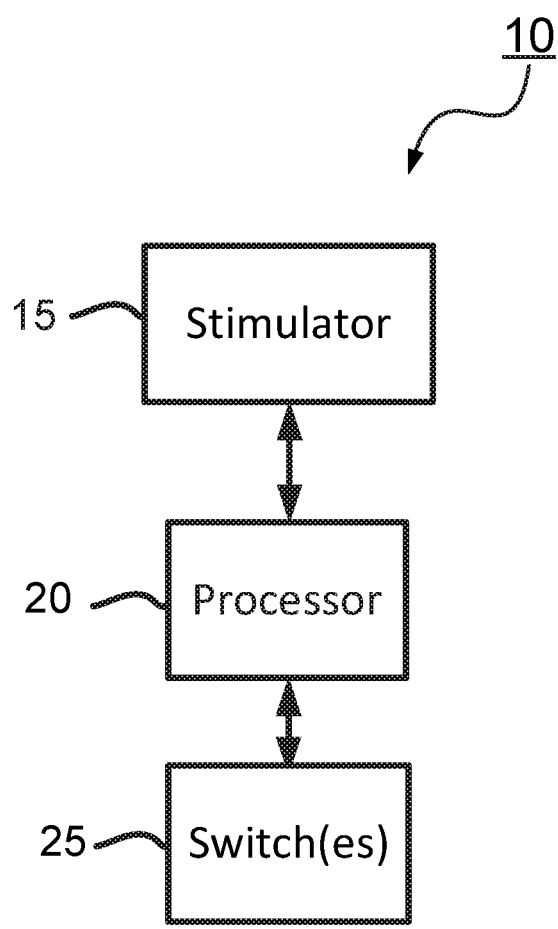
FIG. 5 shows a stimulation system for treating hyperactivity of an eyelid closing muscle according to embodiments of the present invention.
Figure 6:
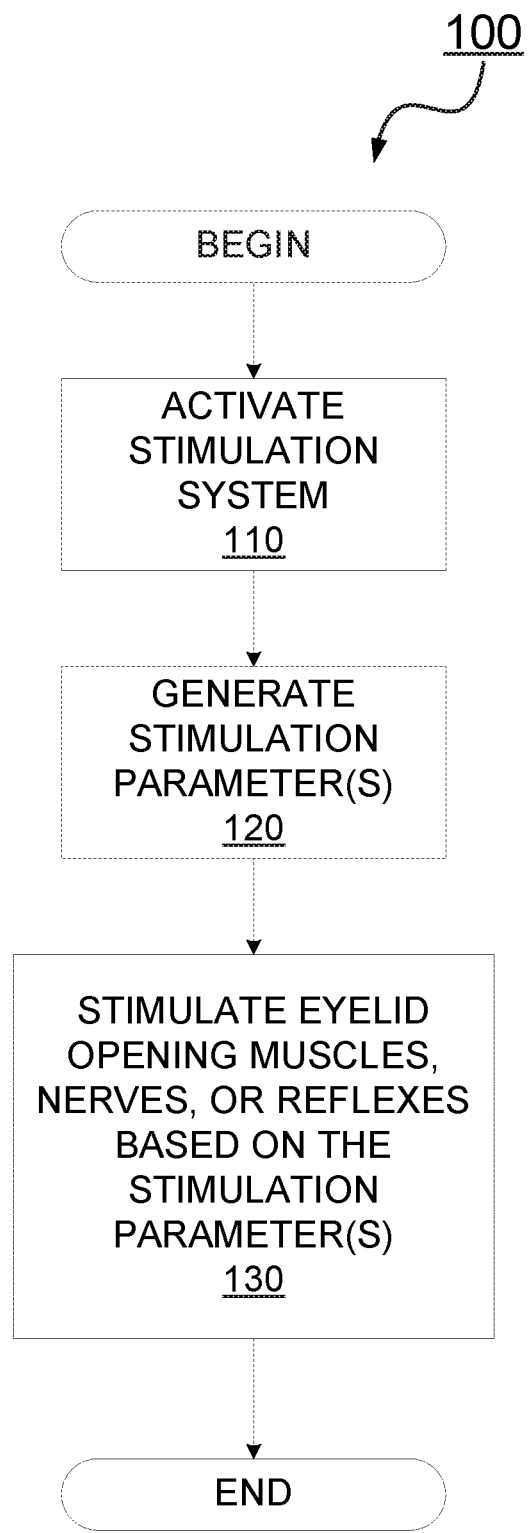
FIG. 6 shows a process of treating hyperactivity of an eyelid closing muscle according to embodiments of the present invention.

FIGS. 5 and 6 show a stimulation system 10 and method 100, respectively, for treating hyperactivity of an eyelid closing muscle according to embodiments of the present invention. The stimulation system 10 includes one or more stimulators 15 and a processor 20, in communication with the stimulator 15, which may include a pulse generator. As mentioned above, the stimulation may be electrical, mechanical, and/or vibratory stimulation. For example, the stimulator may be a stimulating electrode, e.g., a 1 mm stimulating electrode.

In some embodiments, the stimulation system 10 further includes an activating switch 25 that activates the stimulation system. The activating switch 25 may automatically activate the stimulation system 10 based on various sensed parameters or may manually activate the system, e.g., through the use of a manual activator, operable by the subject, e.g., a switch or toggle. For example, the activating switch 25 may be a sensing electrode configured to sense the activity of an eyelid closing muscle and the stimulator 15 is configured to stimulate the eyelid opening muscles or innervating nerves, the eyelid opening reflexes in muscles, and/or the eyelid opening reflexes in non-muscular tissue, based on the sensed activity. The stimulator(s) 15 may be placed near or in contact with the eyelid opening muscles or innervating nerves, the eyelid opening reflexes in muscles, and/or the eyelid opening reflexes in non-muscular tissue.

Embodiments of the present invention may be totally or partially implanted in the subject. For example, the stimulator may include a housing that can be very small with all of the implant's electronic components contained in a robust and compact hermetically sealed case. Energy and necessary information may be inductively or optically transferred through the skin of the subject. This can be achieved by either enclosing the electronic circuitry inside a metallic case with a secondary coil placed aside or around the case. Similarly, this may be achieved by enclosing the electronic circuitry and a secondary coil inside a dielectric case.

Once the stimulation system is activated (step 110), the processor 20 generates at least one stimulation parameter that is used to stimulate the eyelid opening muscles, nerves, and/or reflexes (step 120). For example, the stimulation parameter may be a biphase current pulse, and the biphase current pulse may have a duration of about 0.001 ms to 50 ms, in most subjects from about 0.1 msec to 5 msec, and a magnitude in the range of about 0.05 mA to 20 mA, in most subjects from about 0.5 mA to 5 mA. The stimulation parameter may be a frequency and/or amplitude of vibration, and the stimulator may be a vibration generator, such as a piezoelectric actuator, an electrodynamic actuator and/or a mechanical actuator.

The stimulation parameter from the processor 20 is received by the one or more stimulators 15, and the stimulator stimulates the eyelid opening muscles or innervating nerves, the eyelid opening reflexes in muscles, and/or the eyelid opening reflexes in non-muscular tissue, based on the stimulation parameter (step 130).

Some embodiments of the processor 20 may be implemented as hardware, software (e.g., a computer program product), or a combination of both software and hardware. For example, embodiments may be implemented as a computer program product for use with a computer system. Such implementation may include a series of computer instructions or program code fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions may embody all or part of the functionality previously described herein with respect to the processor. Those skilled in the art should appreciate that such computer instructions may be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web).

While the invention has been described in connection with specific embodiments thereof, it will be understood that it is capable of further modification. This application is intended to cover any variation, uses, or adaptions of the invention and including such departures from the present disclosure as come within known or customary practice in the art to which invention pertains.

What is claimed is:

1. A stimulation system for treating hyperactivity of an eyelid closing muscle in a subject, the system comprising:
   an activating switch configured to generate a first signal, wherein the activating switch includes a sensing electrode configured to detect activity of the eyelid closing muscle in an eye and to generate the first signal based on the detected activity;
   a processor, in communication with the activating switch, configured to generate at least one stimulation parameter, based on the first signal, in order to stimulate one or more eyelid opening muscles or innervating nerves of the subject; and
   a stimulator configured to receive the at least one stimulation parameter and to selectively activate the one or more eyelid opening muscles or innervating nerves of the subject in the same eye based on the at least one stimulation parameter, without activating the eyelid closing muscle in the subject.

2. The system according to claim 1, wherein the activating switch is a manual activator configured to generate the first signal when operated by the subject.

3. The system according to claim 1, wherein the activating switch automatically generates the first signal based on sensed parameters.

4. The system according to claim 1, wherein the activating switch is a manual activator configured to generate the first signal when manually operated by the subject.

5. The system according to claim 1, wherein the stimulator is configured to selectively stimulate the one or more eyelid opening muscles or innervating nerves using electrical stimulation, mechanical stimulation, vibratory stimulation, or combinations thereof.

6. The system according to claim 1, wherein the stimulator is a vibration generator configured to stimulate the one or more eyelid opening muscles or innervating nerves of the subject.

7. The system according to claim 6, wherein the vibration generator is a piezoelectric actuator, an electrodynamic actuator, a mechanical actuator, or combinations thereof.

* * * * *